US005567586A

United States Patent [19]
Croce

[11] Patent Number: 5,567,586
[45] Date of Patent: Oct. 22, 1996

[54] METHODS OF INDENTIFYING SOLID TUMORS WITH CHROMOSOME ABNORMALITIES IN THE ALL-1 REGION

[75] Inventor: Carlo M. Croce, Philadelphia, Pa.

[73] Assignee: Thomas Jefferson University, Philadelphia, Pa.

[21] Appl. No.: 446,926

[22] Filed: May 18, 1995

[51] Int. Cl.$^6$ .............................. C12Q 1/68; C12P 19/34; C07H 21/02; C07H 21/04
[52] U.S. Cl. .......................... 435/6; 435/91.2; 536/23.1; 536/24.3; 536/24.31; 536/24.33
[58] Field of Search ..................... 435/6, 91.2; 536/23.1, 536/24.3–.33

[56] References Cited

FOREIGN PATENT DOCUMENTS

WO93/12136   6/1993   WIPO.
WO94/26930   11/1994  WIPO.

OTHER PUBLICATIONS

Cimino et al, Cancer Research 51:6712–6714.
Solomon Science 254:1153–1160, 1991.
Kobayashi, Genes, Chromosomes and Cancer 8:246–252, 1993.
Bowden, D. et al., "Studies on Locus Expression, Library Representation, and Chromosome Walking Using an Efficient Method to Screen Cosmid Libraries", *Gene* 1988, 71, 391–400.
Chen, C. et al., "Breakpoint Clustering in t(4;11) (q21;23) Acute Leukemia", *Blood* 1991, 78, 2498–2504.
Chomczynski, P. and Sacchi, "Single–Step Method of RNA Isolation by Acid Guanidinum Thiocyanate–Phenol–Chloroform Extraction", *Analytical Biochem.* 1987, 162, 156–159.
Cimino, G. et al., "Cloning of ALL-1, the Locus Involved in Leukemias with the t(4;11) (q21;q23), t(9;11) (p22;q23), and t(11;19) (q23;p13) Chromosome Translocations", *Cancer Res.* 1991, 51, 6712–6714.
Croce, C., "Role of Chromosome Translocations in Human Neoplasia", *Cell* 1987, 49, 155–156.
Gu, Y. et al., "Sequence Analysis of the Breakpoint Cluster Region in the ALL-1 Gene Involved in Acute Leukemia", *Cancer Research* 1994, 54, 2327–2330.
Gu, Y. et al., "The t(4;11) Chromosome Translocation of Human Acute Leukemias Fuses the ALL-1 Gene, Related to Drosophia *trithorax*, to the AF-4 Gene", *Cell* 1992, 71, 701–708.
Haluska, F. et al., "Localization of the Human Jun Protooncogene to Chromosome Region 1p31–32", *PNAS USA* 1988, 85, 2215–2218.
Herlyn, M. et al., "Characteristics of Cultured Human Melanocytes Isolated from Different Stages of Tumor Progression", *Cancer Research* 1985, 45, 5670–5676.

Huebner, K. et al., "Twenty–seven Nonoverlapping Zinc Finger cDNAs from Human T Cells Map to Nine Different Chromosomes with Apparent Clustering", *Am. J. Hum. Genet.* 1991, 48, 726–740.
Linnenbach, A. et al., "Structural Aleration in the MYB Protooncogene and Deletion Within the Gene Encoding α–type Protein Kinase C in Human Melanoma Cell Lines", *PNAS USA* 1988, 85, 74–78.
Morris, S. et al., "Reassignment of the Human ARH9 RAS–Related Gene to Chromosome 1p13–p21", *Genomics* 1993, 15, 677–679.
Nakamura, T. et al., "Genes on Chromosomes 4, 9, and 19 Involved in 11q23 Abnormalities in Acute Leukemia Share Sequence Homology an/or Common Motifs", *PNAS USA* 1993, 90, 4631–4635.
Rowley, J. et al., "Mapping Chromosome Band 11q23 in Human Acute Leukemia with Biotinylated Probes: Identification of 11q23 Translocation Breakpoints with a Yeast Artificial Chromosome", *PNAS USA* 1990, 87, 9358–9362.
Sacchi, N. et al., "Hu–ets–1 and Hu–ets–2 Genes are Transposed in Acute Leukemias with (4;11) and (8;21) Translocations", *Science* 1986, 231, 379–382.
Schichman, S. et al., "ALL–1 Partial Duplication in Acute Leukemia", *PNAS USA* 1994, 91, 6236–6239.
Schichman, S. et al., "ALL–1 Tandem Duplication in Acute Myeloid Leukemia with a Normal Karyotype Involves Homologous Recombination Between Alu Elements", *Cancer Res.* 1994, 54, 4277–4280.
Shtivelman, "Fused Transcript of abl and bcr Genes in Chronic Myelogenous Leukaemia", *Nature* 1985, 315, 550–554.
Solomon, E. et al., "Chromosome Aberrations and Cancer", *Science* 1991, 254, 1153–1160.
U.S. Ser. No. 07/805,093 Dec. 11, 1991.
U.S. Ser. No. 07/888,839 May 27, 1992.
U.S. Ser. No. 07/971,094 Oct. 30, 1992.
U.S. Ser. No. 08/062,443 May 14, 1993.
U.S. Ser. No. 08/320,559 Oct. 11, 1994.
U.S. Ser. No. 08/327,392 Oct. 19, 1994.

*Primary Examiner*—Stephanie W. Zitomer
*Assistant Examiner*—Dianne Rees
*Attorney, Agent, or Firm*—Woodcock Washburn Kurtz Mackiewicz & Norris

[57] ABSTRACT

Methods of determining whether a solid tumor has an ALL-1 gene rearrangement or an ALL-1 gene mutation are disclosed. The methods comprise the steps of obtaining a sample of a solid tumor and detecting the presence of an ALL-1 gene rearrangement or mutation in a cell in said sample. ALL-1 gene rearrangements and mutations are detected by Southern blot analysis, PCR amplification analysis, in situ hybridization analysis, Northern blot analysis or DNA sequence analysis.

23 Claims, No Drawings ved with the t(X;18)(p11.2;q11.2) chromosome translocations; the TLS-CHOP fusion gene found in myxoid liposarcoma with t(12;16)(q13;p11); and the fusion of the PAX-3 homeotic gene with the FKHR gene in t(2;13)(q35;q14) translocations involved in alveolar rhabdomyosarcoma.

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
      ( A ) LENGTH: 20
      ( B ) TYPE: nucleic acid
      ( C ) STRANDEDNESS: single
      ( D ) TOPOLOGY: linear ( x i ) SEQUENCE DESCRIPTION: SEQ ID NO:1:

AGGAGAGAGT TTACCTGCTC                    20

( 2 ) INFORMATION FOR SEQ ID NO:2:

( i ) SEQUENCE CHARACTERISTICS:
      ( A ) LENGTH: 20
      ( B ) TYPE: nucleic acid
      ( C ) STRANDEDNESS: single
      ( D ) TOPOLOGY: linear ( x i ) SEQUENCE DESCRIPTION: SEQ ID NO:2:

GGAAGTCAAG CAAGCAGGTC                    20

( 2 ) INFORMATION FOR SEQ ID NO:3:

( i ) SEQUENCE CHARACTERISTICS:
      ( A ) LENGTH: 20
      ( B ) TYPE: nucleic acid
      ( C ) STRANDEDNESS: single
      ( D ) TOPOLOGY: linear ( x i ) SEQUENCE DESCRIPTION: SEQ ID NO:3:

GTCCAGAGCA GAGCAAACAG                    20

( 2 ) INFORMATION FOR SEQ ID NO:4:

( i ) SEQUENCE CHARACTERISTICS:
      ( A ) LENGTH: 20
      ( B ) TYPE: nucleic acid
      ( C ) STRANDEDNESS: single
      ( D ) TOPOLOGY: linear ( x i ) SEQUENCE DESCRIPTION: SEQ ID NO:4:

ACACAGATGG ATCTGAGAGG                    20

( 2 ) INFORMATION FOR SEQ ID NO:5:

( i ) SEQUENCE CHARACTERISTICS:
      ( A ) LENGTH: 22
      ( B ) TYPE: nucleic acid
      ( C ) STRANDEDNESS: single
      ( D ) TOPOLOGY: linear ( x i ) SEQUENCE DESCRIPTION: SEQ ID NO:5:

GCTCTCAGGC CTTTCCTTCT TC                 22

( 2 ) INFORMATION FOR SEQ ID NO:6:

( i ) SEQUENCE CHARACTERISTICS:
      ( A ) LENGTH: 21
      ( B ) TYPE: nucleic acid
      ( C ) STRANDEDNESS: single
      ( D ) TOPOLOGY: linear ( x i ) SEQUENCE DESCRIPTION: SEQ ID NO:6:

TTCCCATCGC TCTTTCCCAA G  21

METHODS OF INDENTIFYING SOLID TUMORS WITH CHROMOSOME ABNORMALITIES IN THE ALL-1 REGION

ACKNOWLEDGEMENT OF GOVERNMENT RIGHTS

This invention was made with Government support under grant number CA 39860 awarded by the National Institutes of Health. The Government has certain rights in this invention.

FIELD OF THE INVENTION

The present invention relates to methods of identifying chromosomal translocations and genetic rearrangements involving the ALL-1 gene in solid tumors and to diagnostic kits for performing such methods.

BACKGROUND OF THE INVENTION

Genetic studies have revealed that genetic rearrangements resulting in loss of function, such as deletions, are the most frequent alterations in solid tumors. Chromosome translocations accompanied by oncogene activation, have, however, also been described frequently in soft tissues sarcomas. For example, in Ewing's sarcoma and in primitive neuroectodermal tumors (PNET), the EWS gene at band 22q12 fuses either with the FLI-1 gene at band 11q24 or with the ERG gene at band 21q22, leading to the formation of a chimeric transforming genes. Other examples include: the SYT-SSX gene fusion in synovial sarcomas with the t(X;18)(p11.2;q11.2) chromosome translocations; the TLS-CHOP fusion gene found in myxoid liposarcoma with t(12;16)(q13;p11); and the fusion of the PAX-3 homeotic gene with the FKHR gene in t(2;13)(q35;q14) translocations involved in alveolar rhabdomyosarcoma.

The molecular characterization of the t(1;17) and t(17;22) translocations in neurofibromatosis type 1 has led to the cloning of the NF1 gene, encoding neurofibromin, a protein that downregulates p21ras. Additional studies demonstrated that the NF1 gene is a tumor suppressor gene. In fact, mutations of the NF1 gene that cause familial neurofibromatosis, also occur in somatic cells and can lead to the development of tumors such as colon adenocarcinoma, myelodysplastic syndrome and anaplastic astrocytoma.

The characterization of genetic rearrangements associated with solid tumors is relevant to the diagnosis of disease, prognosis of likely outcome and determination of therapeutic action. The genetic basis for a tumorigenic phenotype indicates the nature of the tumor, its likely aggressiveness and its likelihood to respond to various modes of therapeutic intervention.

Accordingly, there is a need for reagents, kits and methods for screening tissue for genetic rearrangements involving the ALL-1 gene. There is a need for reagents, kits and methods for identifying solid tumors which contain genetic rearrangements involving the ALL-1 gene.

SUMMARY OF THE INVENTION

The present invention relates to methods of determining whether a solid tumor has an ALL-1 gene rearrangement or mutation. The methods comprise the steps of obtaining a sample of a solid tumor and detecting the presence of an ALL-1 gene rearrangement or mutation in a cell in said sample. ALL-1 gene rearrangements and mutations are detected by Southern blot analysis, PCR amplification analysis, in situ hybridization analysis, Northern blot analysis or DNA sequencing methodology.

DETAILED DESCRIPTION OF THE INVENTION

It has been discovered that, in addition to playing a major role in human acute leukemias, rearrangements involving ALL-1 are also involved in the pathogenesis of solid tumors. The discovery allows for the identification of solid tumors which have ALL-1 rearrangements. The genetic characterization of a solid tumor is useful to differentiate solid tumors that have ALL-1 rearrangements or mutations from solid tumors that do not have ALL-1 rearrangements or mutations. By identifying solid tumors that have ALL-1 rearrangements, other genetic bases for the transformed phenotype can be eliminated from the diagnosis. The genetic characterization of solid tumors is useful in the diagnosis of disease, prognosis of the patient's prospect for recovery and determination of appropriate therapeutic action. The identification of the genetic basis for the transformed phenotype of a solid tumor is useful in assessing the course of action which is indicated by the individual's illness.

The ALL-1 gene, located at human chromosome 11 band q23, is involved in chromosome translocations associated with de novo and secondary acute lymphoblastic leukemias (ALL) and acute myeloid leukemias (AML). Approximately 80% of infant ALL, 60% of infant AML and 6% of ALL and AML in older children and adults show cytogenetic abnormalities at 11q23. In addition, more than 75% of secondary leukemias associated with therapy with inhibitors of topoisomerase II show alterations at 11q23 and ALL-1 gene rearrangements.

In leukemias with translocations involving 11q23, the ALL-1 gene fuses with one of many different genes. In fact, at least 20 different reciprocal translocations involving band 11q23 have been described. Some of the ALL-1 partner genes have been cloned and characterized: AF1p from chromosome 1; AF4 from chromosome 4; AF6 from chromosome 6; AF9 from chromosome 9; AF17 from chromosome 17; ENL from chromosome 19 and AFX from human chromosome X. Among these different genes, only AF9 and ENL share sequence homology.

Recently, by examining specimens from patients with AML without chromosome translocations, it has been discovered that the ALL-1 gene may undergo self fusion resulting in a partially duplicated gene and a transcript with an in-frame fusion of either exon 6 or exon 8 with exon 2. This observation suggests that an alteration of the ALL-1 protein product is the critical event in the oncogenic conversion of ALL-1 gene, while fusion partners might not play an important role in the oncogenic process.

A cell line derived from a gastric carcinoma that lacks cytogenetic evidence of chromosome 11q23 translocations (Mgc80-3) has been found to possess an ALL-1 gene rearrangement. The molecular analysis of this rearrangement shows a partially duplicated ALL-1 gene, similar to the rearrangement observed in acute leukemias without cytogenetic 11q23 alterations. The discovery disclosed herein, that the ALL-1 gene is involved in the pathogenesis of solid tumors provides a means to characterize the genetic nature of solid tumors and thereby determine the diagnosis, prognosis and optimum course of treatment.

Some aspects of the present invention include various methods of determining whether a solid tumor has an ALL-1 gene rearrangement or mutation by sequence-based molecular analysis. Several different methods are available for doing so including: 1) Southern blot analysis, 2) Northern Blot analysis, 3) Polymerase Chain Reaction (PCR) technology, 4) in situ hybridization technology and DNA sequencing technology. Furthermore, the invention relates to probes, primers and reagents used in the methods of identifying ALL-1 gene rearrangements in solid tumor cells. In addition, the invention relates to diagnostic kits which comprise components for identifying ALL-1 gene rearrangements in solid tumor cells.

Solid tumor cells with ALL-1 gene rearrangements can be distinguished from solid tumor cells without ALL-1 gene rearrangements in solid tumor cells by identifying genetic rearrangements at the ALL-1 locus or the presence of hybrid proteins which include portions of the normal ALL-1 gene product. ALL-1 gene mutations can be identified by DNA sequence analysis.

The genomic sequence of the breakpoint region of the ALL-1 gene on chromosome 11 is disclosed in Gu, Y. et. al. (1994) *Cancer Research* 54:2327–2330, which is incorporated herein by reference. The cDNA sequence of the ALL-1 gene is disclosed in Gu, Y. et. al. (1992) Cell 71:701–708, which is incorporated herein by reference. In addition, genomic and cDNA sequences as well as probes and primers are disclosed in U.S. Ser. No. 07/805,093 filed Dec. 11, 1991, U.S. Ser. No. 07/888,839 filed May 27, 1992, U.S. Ser. No. 07/971,094 filed Oct. 30, 1992, PCT patent application PCT/US92/10930 filed Dec. 9, 1992, U.S. Ser. No. 08/062, 443 filed May 14, 1993, PCT patent application PCT/US94/ 04496 filed Apr. 22, 1994, U.S. Ser. No. 08/320,559 filed Oct. 11, 1994, and U.S. Ser. No. 08/327,392 filed Oct. 19, 1994, which are each incorporated herein by reference.

Probes are provided for detecting chromosome abnormalities involving the ALL-1 gene, including probes for detecting chimeric genes generated by translocations.

The ALL-1 gene located at human chromosome 11 band q23 is rearranged in some solid tumors with interstitial deletions or reciprocal translocations between this region and chromosomes 1, 2, 4, 6, 9, 10, 15, 17 or 19. The gene spans approximately 100 kb of DNA and contains at least 21 exons. It encodes a protein of approximately 4,000 amino acids containing three regions with homology to sequences within the Drosophila trithorax gene including cysteine-rich regions which can be folded into six zinc finger-like domains. The breakpoint cluster region within ALL-1 spans approximately 8 kb and encompasses several small exons (including exons 5–10), most of which begin in the same phase of the open reading frame.

The preferred method of determining whether a solid tumor cell has an ALL-1 rearrangement is to perform Southern blot analysis of genomic DNA. Genomic DNA is extracted from cells in a sample from a solid tumor and cut with one or more restriction endonucleases. The DNA fragments that are generated are separated in an electrophoresis matrix and transferred to a solid phase support such as a membrane or paper. The DNA fixed to the solid support is contacted with a detectable probe that hybridizes to ALL-1 sequences including those in the breakpoint region of the gene. Accordingly, the probe will hybridize to the corresponding fragments that were generated by the enzyme digest and the location of the detectable probe hybridized to the corresponding fragment can be identified. If the ALL-1 gene has been rearranged, the fragments that were generated by the enzyme digest will be of a different size than the fragments that were generated by the enzyme digest of DNA from cells without ALL-1 rearrangements. In preferred embodiments, different lanes of an electrophoresis matrix that is used to separate DNA fragments include a lane that has a sample of size marker DNA, a lane that has a sample of digested DNA from solid tumor, and a lane that has a sample of digested DNA from cells known to not have an ALL-1 rearrangement. In some embodiments the probe comprises an isolated fragment of ALL-1 DNA sequences that consists of a specific fragment generated by restriction enzyme digestion. The Southern blot is made using DNA digested with the same restriction enzymes used to make the probe. Thus, the probe will hybridize to a single band of DNA of a known size in samples that do not contain ALL-1 rearrangements.

The techniques for performing Southern blot analyses are well known by those having ordinary skill in the art. (See: Sambrook et al, eds. "Molecular Cloning: A Laboratory Manual" 2nd Edition, Cold Spring Harbor Laboratory Press 1989, and Shtivelman et. al., *Nature* 1985, 315, 550–554, which are each incorporated herein by reference. DNA extraction, restriction enzyme digestion, electrophoresis, Southern blotting, probe preparation and hybridization are all well known techniques that can be routinely performed using readily available starting material.

One having ordinary skill in the art, performing routine techniques, could select enzymes to generate fragments from genomic DNA extracted from a tumor. The fragments are separated by electrophoresis and, for example, transferred to nitrocellulose paper. Labelled probes made from an isolated specific fragment or fragments can be used to visualize the presence of a complementary fragment fixed to the paper.

Using Southern blot analysis, solid tumors can be identified as having rearrangements involving the ALL-1 gene. Labelled nucleic acid molecules that hybridize to ALL-1 sequences can be used to probes Southern blots of restriction enzyme digested genomic DNA samples extracted from cells of solid tumors. The labelled probe will generate a detectable band or bands and the location and/or pattern of the bands can be compared to the location and/or pattern generated when normal DNA is used as a starting material. If the labelled ALL-1 probes generates a banding pattern with the tumor DNA that is different from the banding pattern that is generated using the normal DNA, rearrangement of the ALL-1 gene in the DNA of the solid tumor is indicated.

A single probe or a set of probes may be used in Southern blot analysis. In some embodiments, the probe or probes should hybridize to the entire breakpoint region and, optionally, sequences telomeric to the telomeric boundary of the breakpoint region. In some embodiments, the probe or probes should hybridize to a portion of the breakpoint region including the telomeric boundary and sequences telomeric to the telomeric boundary of the breakpoint region.

Southern blot procedures are well known and can be routinely performed from DNA obtained from patient samples suspected of including cells that have rearranged chromosomes. Those having ordinary skill in the art can readily perform Southern blot analyses using available starting materials.

In some preferred embodiments, probes include nucleic acid molecules that comprise fragments of the ALL-1 cDNA sequence. Probes that include nucleic acid molecules that preferably comprise fragments of ALL-1 cDNA having from at least 20 nucleotides to full length ALL-1 cDNA sequences. In some preferred embodiments, probes include nucleic acid molecules that consist of the full length ALL-1 cDNA sequence. In some preferred embodiments, probes include nucleic acid molecules that comprise or consist of the fragments of the ALL-1 cDNA sequence having 100–10000 nucleotides, preferably 500–5000, in some embodiments 800–3500 nucleotides. In some preferred embodiments, probes include nucleic acid molecules that comprise or consist of the fragments of the ALL-1 cDNA sequence having 100–1000 nucleotides, preferably 400–900, in some embodiments about 800 nucleotides. The breakpoint region roughly corresponds to nucleotides 3550–4430 of the ALL-1 cDNA. Probes preferably contain these sequences and/or additional sequences upstream and/ or downstream. According to one preferred embodiments, the probe is an 859 fragment that corresponds to the 8.3 kb BamHI fragment generated by BamHI digestion of ALL-1 gene. Such a 859 base pair probe spans exons 5–11.

In some preferred embodiments, probes include nucleic acid molecules that consist of the ALL-1 genomic sequences including the ALL-1 breakpoint region. In some preferred embodiments, probes include nucleic acid molecules that consist of the ALL-1 genomic sequences including the ALL-1 breakpoint region having 100–8000 nucleotides, preferably 500–5000, in some embodiments 800–3500 nucleotides. Genomic sequences may be inserted into vectors such as cosmids or YACs. In one embodiment, a 0.7 kb DdeI fragment of ALL-1 inserted into a cosmid, termed cosmid 53, is useful to detect ALL-1 rearrangements, particularly, rearranged fragments in tumor DNAs digested with EcoRV, XbaI, or BamHI. In another embodiment, a 289 base pair fragment of ALL-1 intron 1 is used as a probe. This probe, which is called SAS1, is derived from an XhoI/HindIII fragment by PCR (Schichman, S. A. et. al. (1994) *Proc. Natl. Acad. Sci. USA* 91:6236–6239, which is incorporated herein by reference).

Probes are preferably labelled. In some preferred embodiments, probes are radiolabelled. In some preferred embodiments, probes are biotinylated. Those having ordinary skill in the art can readily employ any of several well known techniques for making and using detectable probes that hybridize to nucleic acid molecules.

According to the invention, diagnostic kits can be assembled which are useful to practice methods of distinguishing solid tumors with ALL-1 rearrangements from solid tumors without ALL-1 rearrangements by Southern blot analysis. Such diagnostic kits comprise cloned DNA fragments which are useful as probes for performing Southern blots analysis of DNA extracted from cells. Accordingly, diagnostic kits of the present invention comprise a cloned DNA fragment of the ALL-1 gene. The probes are preferably labelled, most preferably labelled with a radioisotope. The diagnostic kits according to the present invention may further comprise a negative control to be run as a standard. The negative control is a DNA sample that produces the hybridization pattern expected if translocation has not taken place. Thus, the pattern produced by the sample being tested can be compared side by side with the control. One would use genomic DNA from the patient's normal tissue as a negative control. If the pattern produced by the sample being tested is substantially identical to the control pattern, an ALL-1 rearrangement is not indicated. If the pattern produced by the sample being tested is dissimilar to the control pattern, an ALL-1 rearrangement is indicated.

Northern blot analysis is similar to Southern Blot analysis except that RNA is isolated and separated on gels rather than enzyme digested chromosomal DNA. Probes that are particularly useful in Northern blot analysis include cDNA and fragments thereof. In some preferred embodiments, probes include nucleic acid molecules that consist of the cDNA sequences. Northern analyses are performed as described in Shtivelman et. al., *Nature* 1985, 315, 550–554, which is incorporated herein by reference.

Another method to identify solid tumors with ALL-1 translocations is to detect the presence of specific DNA sequences in genetic material derived from cells suspected of being ALL-1 solid tumors using polymerase chain reaction (PCR) technology. PCR technology is practiced routinely by those having ordinary skill in the art and its uses in diagnostics are well known and accepted. Methods for practicing PCR technology are disclosed in "PCR Protocols: A Guide to Methods and Applications", Innis, M. A., et. al. Eds. Academic Press, Inc. San Diego, Calif. (1990) which is incorporated herein by reference. Applications of PCR technology are disclosed in "Polymerase Chain Reaction" Erlich, H. A., et. al., Eds. Cold Spring Harbor Press, Cold Spring Harbor, N.Y. (1989) which is incorporated herein by reference.

In the present invention, ALL-1 rearrangements can be identified by detecting a chimeric gene that results from the ALL-1 gene translocating to one of the several chromosomes known to be involved in ALL-1 translocations. This is accomplished performing PCR on a sample of genetic material derived from cells suspected of having an ALL-1 translocation using PCR primers that hybridize to the 5' end of ALL-1 gene and the 3' end of a partner gene from one of the chromosomes with which ALL-1 is known to form rearrangements with. Alternatively, PCR primers may be used that hybridize to the 3' end of ALL-1 gene and the 5' end of a partner gene from one of the chromosomes with which ALL-1 is known to form rearrangements with. If a chimeric gene is present which is formed by ALL-1 translocating with one of the chromosomes that comprises a partner gene, it will be amplified. Various partner gene sequences and primers for preparing primer sets, methods and kits for PCR analysis to detect ALL-1 rearrangements are disclosed in U.S. Ser. No. 07/805,093 filed Dec. 11, 1991, U.S. Ser. No. 07/888,839 filed May 27, 1992, U.S. Ser. No. 07/971,094 filed Oct. 30, 1992, PCT patent application PCT/US92/10930 filed Dec. 9, 1992, U.S. Ser. No. 08/062,443 filed May 14, 1993, PCT patent application PCT/US94/04496 filed Apr. 22, 1994, U.S. Ser. No. 08/320,559 filed Oct. 11, 1994, and U.S. Ser. No. 08/327,392 filed Oct. 19, 1994, which are each incorporated herein by reference.

To perform this method, RNA is extracted from tumor cells and used to make cDNA using well known methods and readily available starting materials. PCR can be performed on genomic DNA instead of cDNA derived from RNA. It is easier and preferred to use cDNA although it is technically possible and therefore contemplated that the method can be performed using genomic DNA.

The cDNA is combined with the one primer for ALL-1 and one or more primers for partner genes. In addition, free nucleotides and enzyme are provided following standard PCR protocols. The mixture undergoes a series of temperature changes. If the cDNA of a chimeric gene is present, that is, if primers hybridize to sequences on the same molecule, the molecule comprising the primers and the intervening complementary sequences will be exponentially amplified. The amplified DNA can be easily detected by a variety of well known means. If the chimeric gene is not present, no DNA molecule will be exponentially amplified. The PCR technology therefore provides an extremely easy, straightforward and reliable method of detecting the chimeric gene.

If the chimeric gene is present, multiple copies of the cDNA transcribed from it will be made. If the chimeric gene is not present, PCR will not generate a discrete detectable product. Amplified DNA may be detected by several well known means. The preferred method for detecting the presence of amplified DNA is to separate the PCR reaction material by gel electrophoresis and stain the gel with ethidium bromide in order to visual the amplified DNA if present. A size standard of the expected size of the amplified DNA is preferably run on the gel as a control.

In some instances, such as when unusually small amounts of RNA are recovered and only small amounts of cDNA are generated therefrom, it is desirable or necessary to perform a PCR reaction on the first PCR reaction product. That is, if difficult to detect quantities of amplified DNA are produced by the first set of reactions, a second set of PCR reactions can be performed to make multiple copies of DNA sequences of the first amplified DNA. A nested set of primers are used in the second PCR reaction. The nested set of primers hybridize to sequences downstream of the 5' primer and upstream of the 3' primer used in the first reaction.

In addition to diagnosis, the PCR methodology and PCR-based kits are particularly useful for monitoring the disease once the diagnosis is established. In particular, the sensitivity of the PCR assay permits detection of small amounts of tumor for purposes of staging the patient, determining response to therapy and predicting early relapse.

Another method of detecting the presence of specific DNA sequences is by in situ hybridization technology. In situ hybridization technology is well known by those having ordinary skill in the art. Briefly, detectable probes which contain a specific DNA sequence are added to fixed cells or isolated nuclei. If the cells contain complementary nucleotide sequences, the probes, which can be detected, will hybridize to them. One having ordinary skill in the art, using the genomic sequence information of ALL-1 can devise variety of protocols that use in situ hybridization technology to identify ALL-1 rearrangements ion solid tumor cells.

According to a preferred method of using in situ hybridization techniques to identify whether of not a solid tumor cell has an ALL-1 rearrangement, sets of probes are provided which comprise at least two probes that hybridize to different sequences of the ALL-1 gene; one probe hybridizes to sequences 5' of the breakpoint region, and one probe hybridizes to sequence 3' of the breakpoint region. Thus, if no translocation has occurred, the probes will hybridize adjacent to one another on the same chromosome. Fluorescent probes will appear as a single spot. If a translocation has occurred, the probes will hybridize to sequences on different chromosomes. Fluorescent probes will appear as two distinct spots.

According to another preferred method of using in situ hybridization techniques to identify whether of not a solid tumor cell has an ALL-1 rearrangement, sets of probes are provided which comprise at least one probe that hybridizes to the ALL-1 gene telomeric of the breakpoint region and one probe that hybridizes to chromosome 11 centromere. If no translocation has occurred, the probes will hybridize adjacent to one another on the same chromosome. Fluorescent probes will appear as a single spot. If a translocation has occurred, the probes will hybridize to sequences on different chromosomes. Fluorescent probes will appear as two distinct spots.

For in situ hybridization, it is preferred that very large cloned fragments are used as probes. A common procedure is to label probe with biotin-modified nucleotide and then detect with fluorescently tagged avidin. Hence, probe does not itself have to be labelled with florescent but can be subsequently detected with florescent marker.

Cells are fixed or their nuclei are isolated and the probes are added to the genetic material. It is not necessary that the chromosome be visibly identifiable as in a karyotype. Probes will hybridize to the complementary nucleic acid sequences present in the sample. Using a fluorescent microscope, the probes can be visualized by their fluorescent markers.

In some embodiments, the two different probes are labelled with different colors. If the probes are visible as being very close to each other, the colors of the label will likely blend and appear as an intermediate color of the two used.

According to the invention, diagnostic kits can be assembled which are useful to practice in situ hybridization methods of distinguishing solid tumors with ALL-1 translocations from solid tumors without ALL-1 translocations. Such diagnostic kits comprise a set of labelled fragments which are useful as probes for performing in situ hybridization methods. Accordingly, some diagnostic kits of the present invention comprise a set of labelled probes that include one probe that hybridizes to sequences 5' of the breakpoint region, and one probe that hybridizes to sequence 3' of the breakpoint region. Some diagnostic kits of the present invention comprise a set of labelled probes that comprise at least one probe that hybridizes to the ALL-1 gene telomeric of the breakpoint region and one probe that hybridizes to chromosome 11 centromere. The present invention includes labelled cloned fragments which are useful as probes for performing in situ methods. The labelled probes of the present invention are preferably labelled with fluorescent markers.

The present invention provides methods of identifying solid tumors that have ALL-1 rearrangements by providing a sample of tissue such as a biopsy sample of tissue obtained from a person suspected of having a solid tumor and determining if there are breakpoints on chromosome 11 in the ALL-1 locus. Part or all of the ALL-1 cDNA sequence may be used to create a probe capable of detecting aberrant transcripts resulting from chromosome 11 translocations. The EcoRI probe, for example, was derived from a genomic clone but its location lies within an exon.

Probes useful as diagnostics can be used not only to diagnose the onset of illness in a patient, but may also be used to assess the status of a patient who may or may not be in remission. It is believed that emergence of a patient from remission is characterized by the presence of cells containing ALL-1 abnormalities. Thus, patients believed to be in remission may be monitored using the probes of the invention to determine their status regarding progression or remission from disease. Use of such probes will thus provide a highly sensitive assay the results of which may be used by physicians in their overall assessment and management of the patient's illness.

The present invention provides methods of identifying solid tumors that have ALL-1 mutations by providing a sample of tissue such as a biopsy sample of tissue obtained from a person suspected of having a solid tumor and determining if there are sequence alteration in the ALL-1 gene relative to the sequences of a normal ALL-1 gene in that individual.

In the experiments described below, in Mgc-80-3 cells the absence of the normal transcript in association with the loss-of-heterozygosity studies on chromosome 11q23 seen in solid tumors, suggests that ALL-1 is involved in tumorigenesis by a loss-of-function mechanism. Although chromosome translocations are usually associated with activation of oncogenes, the NF1 gene on chromosome 17q11.2 represents an example of a tumor-suppressed gene that can be knocked out by chromosomal translocations involving band 17q11.2. Additional studies, however, have demonstrated that point mutations are the most frequent genetic changes involving the NF1 gene, leading to loss of NF1 function. It has also been demonstrated that the disruption of the RB1 locus by chromosomal translocation at 13q14.2 represents a predisposing mutation in some retinoblastoma cases. The ALL-1 gene may play a role in some malignant transformation of cells of solid tissues, such as carcinomas.

Loss of heterozygosity (LOH) studies have revealed that region 11q22-q24 is frequently deleted in colon, cervical, breast and ovary carcinomas, and melanoma. In some cases the narrowed region of LOH does not include the ALL-1 locus; however, these results do not rule out the possibility that a region including the ALL-1 gene might also be a target of LOH, independent of the region D11S35-D11S29 recently identified. Marker D11S528, which is telomeric to D11S29 where ALL-1 maps, has been shown to have a frequency of LOH higher than D11S29. Based on the fact that the ALL-1 gene is rearranged in a solid tumor, investigations of LOH at region 11q23-q24 and point mutation analysis of the ALL-1 gene should be performed in carcinomas to assess the role of ALL-1 in these tumors.

Accordingly, another method to identify solid tumors with ALL-1 rearrangements or mutations is to determine DNA sequences in tumor versus normal tissue. ALL-1 exons are amplified using PCR technology or ALL-1 RNA is amplified by RTPCR and the amplified products can be sequenced directly afterward. The methods of amplifying ALL-1 exons or ALL-1 RNA by PCR and RT-PCR, respectively, may be performed using well known techniques by those having ordinary skill in the art. Methods for practicing PCR technology are disclosed in "PCR Protocols: A Guide to Methods and Applications", Innis, M. A., et. al. Eds. Academic Press, Inc. San Diego, Calif. (1990) which is incorporated herein by reference. Applications of PCR technology are disclosed in "Polymerase Chain Reaction" Erlich, H. A., et. al., Eds. Cold Spring Harbor Press, Cold Spring Harbor, N.Y. (1989) which is incorporated herein by reference. PCR primers may be designed using the teachings and sequence information provided herein. DNA sequence analysis is well known and can be routinely performed by those having ordinary skill in the art. (See: Sambrook et al, eds. "Molecular Cloning: A Laboratory Manual" 2nd Edition, Cold Spring Harbor Laboratory Press 1989.) A comparison of the sequence from normal tissue and tumor derived material will indicate whether the tumor cells include DNA with a mutated ALL-1 gene.

To perform this method, RNA is extracted from tumor cells (or normal cells used as controls) and used to make cDNA using well known methods and readily available starting materials. PCR can be performed on genomic DNA instead of cDNA derived from RNA. It is easier and preferred to use cDNA although it is technically possible and therefore contemplated that the method can be performed using genomic DNA. Primers are designed to amplify ALL-1 exons or cDNA sequences and the amplified DNA molecules are sequenced and compared to the normal ALL-1 sequence.

In some instances, such as when unusually small amounts of RNA are recovered and only small amounts of cDNA are generated therefrom, it is desirable or necessary to perform a PCR reaction on the first PCR reaction product. That is, if difficult to detect quantities of amplified DNA are produced by the first set of reactions, a second set of PCR reactions can be performed to make multiple copies of DNA sequences of the first amplified DNA. A nested set of primers are used in the second PCR reaction. The nested set of primers hybridize to sequences downstream of the 5' primer and upstream of the 3' primer used in the first reaction.

In addition to diagnosis, the PCR methodology and PCR-based kits are particularly useful for characterizing the molecular nature of the tumor.

EXAMPLES

Example 1

Materials and Methods

Cell Lines and Rodent-Human Hybrids.

Gastric carcinoma cell lines, Mgc8O-3 and KatoIII (29, 30), were a gift of Dr. Si-Chun Ming. Other cell lines: AGS, RF-1, RF-48, Hs746T (stomach adenocarcinoma); SW48, LoVo, (colon adenocarcinoma); SW1463, SW837 (rectum adenocarcinoma); LNCaP, DU145, PC-3 (prostate adenocarcinoma); NCIH460, A549 (lung cancer); Caov 3 (ovarian carcinoma); JAR (choriocarcinoma); Hep G2 (hepatocarcinoma); 143B (osteogenic sarcoma) and RS 4;11 [ALL with t(4;11)] were obtained from the American Type Culture Collection. Colon adenocarcinoma cell line SW 1222 was provided by Dr. E. Mercer. Melanoma cell lines WM164 and WM793 have been described (Linnenbach, A. J., et. al. (1988) *Proc. Natl. Acad. Sci.* 85, 74–78 and Herlyn, M., et. al. (1985) *Cancer Res.* 45, 5670–5676). Melanoma cell lines SB-1, SB-3, M21 were established in the laboratory of Dr. Soldano Ferrone. Rodent-human hybrid cell lines have been described previously (Huebner, K., et. al. (1991) *Am. J. Hum. Genet.* 48,726–740; Haluska, F., et. al. (1988) *Proc. Natl. Acad. Sci. USA* 85, 2215–2218; Linnenbach, A. J., (1993) *Mol. Cell. Biol.* 31, 1507–1515 and Morris, S., et. al. (1993) *Genomics* 15, 677–679.) or were from the NIGMS Human Genetic Mutant Cell Repository (Coriell Institute, Camden, N.J.). Hybrids retaining partial chromosomes have also been described (Linnenbach, A. J., et. al. (1993) *Mol. Cell. Biol.* 31, 1507–1515 and Morris, S., et. al. (1993) *Genomics* 15, 677–679).

Southern Blot Analysis

Approximately 8 µg of genomic DNA was digested with several restriction enzymes (BamHI, HindIII, EcoRI, BglII, KpnI and XbaI). The digestion products were separated on 0.8% agarose gel, blotted onto positively charged nylon membranes and hybridized (Southern, E. M. (1975) *J. Mol. Biol.* 98, 503–517) with the B859 probe (an 859 bp BamH1 cDNA fragment which spans the ALL-1 breakpoint cluster region between exon 5 and exon 11). The filters that showed rearranged bands with the B859 probe were stripped and probed with SAS1 (a 289 bp DNA probe from intron 1 of the ALL-1 gene).

Northern Blot Analysis

RNA was extracted by the guanidinium thiocyanate method (Chomczynskj, P. & Sacchi, N. (1987) *Anal. Biochem.* 167, 157–159). Aliquots of 10 µh were electrophoresed in 1.1% agarose gel containing formaldehyde, blotted onto nylon membranes and hybridized with the B859 probe.

RT-PCR

Total cDNA from the Mgc8O-3 cell line was prepared with 2 µg of RNA using Superscript Preamplification System for first strand cDNA Synthesis (Gibco BRL). PCR was performed using Taq DNA polymerase (Perkin Elmer Cetus). The following oligonucleotide primers were used:

3.1c 5' AGGAGAGAGTTTACCTGCTC 3' (SEQ ID NO:1) from exon 3, 5.3 5' GGAAGTCAAGCAAGCAGGTC 3' (SEQ ID NO:2) from exon 5, 6.1 5' GTCCAGAGCAGAGCAAACAG 3' (SEQ ID NO:3) from exon 6, and 3.2c 5' ACACAGATGGATCTGAGAGG 3' (SEQ ID NO:4) from exon 3.

The first PCR on the total cDNA was performed with primers 3.1c and 5.3. Nested PCR on 0.5 µl of the first PCR product was performed using as primers 3.2c and 6.1. PCR products were analyzed by agarose gel electrophoresis, subcloned into the TA vector (Invitrogen) and sequenced.

Molecular Cloning

Two bacteriophage libraries were made from size-fractionated EcoRI ( ZAP II) and BglII (EMBL3) digests of the Mgc8O-3 genomic DNA. Recombinants were identified by filter hybridization in the ZAP II library with the B859 probe and in the EMBL 3 library with the SAS1 probe. Construction of the libraries, screening, labeling, hybridization and restriction enzyme mapping were done by standard techniques (Sambrook, J., et. al. (1989) *Molecular cloning: A Laboratory Manual* (Cold Spring Harbor Laboratory press, New York). Positive clones in the ZAP II library were isolated and subcloned into the Bluescript Vector by the in vivo excision protocol (Stratagene). Subclones from the EMBL 3 library were constructed in the pbluescript 11 plasmid vector. All the clones were characterized by Southern blot hybridization and were subsequently mapped and sequenced. PCR amplification using Taq polymerase and Taq Extender PCR additive (Stratagene) was performed in Mgc8O-3 genomic DNA using oligonucleotide primers B1T3-F15' GCTCTCAGGCCTTTCCTTCTTC 3' (SEQ ID NO:5) and 0.9K-F1 5' TTCCCATCGCTCTTTCCCAAG 3' (SEQ ID NO:6).

The PCR product (MCHI) was subcloned in the TA vector and sequenced. All the sequences were determined by cycle sequencing using an Applied Biosystems 373A DNA sequencer. Programs from the Genetics Computer Group were utilized for data analysis.

RESULTS AND DISCUSSION

Twenty six cell lines derived from ten different types of solid neoplasms were examined for ALL-1 rearrangements. A cDNA probe (B859) which spans the ALL-1 breakpoint cluster region involved in acute leukemias was used to detect rearrangements of the ALL-1 gene by Southern blot in these cell lines. A gastric carcinoma cell line (Mgc8O-3) showed rearranged bands following DNA digestion with several enzymes. The presence of an ALL-1 gene rearrangement in the Mgc8O3 cell line was particularly surprising, since the lack of cytogenetic evidence of chromosome 11 abnormalities in this cell line has been previously reported. However, ALL-1 self-fusion and partial duplication in acute myeloid leukemias with a normal karyotype or trisomy 11 has been reported (Schichman, S. A., et. al. (1994) *Proc. Natl. Acad. Sci. USA* 91, 6236–6239; and Schichman, S. A., et. al. (1994) *Cancer Res.* 54, 4277–4280). The genomic DNA of the Mgc8O-3 cell line was examined with a probe (SAS1) which detects rearrangements associated with ALL-1 partial duplication. The SAS1 probe showed rearranged bands on Southern blot, but in contrast with the AMLs mentioned above, these bands did not comigrate with the rearranged bands detected by the B859 probe, with the exception of the KpnI rearranged band. ALL-1 expression in the Mgc8O-3 cell line was also examined using B859 as a probe, by Northern blot analysis. The RNA of a gastric carcinoma cell line with no evidence of ALL-1 alterations (KatoIII) and the RS 4:11 cell line which contains a t(4,11) chromosomal translocation and shows two transcripts of the approximate size of 15 kb and 12.7 kb were used as controls. Only an ~18 kb altered transcript was detected, indicating expression of an altered ALL-1 gene and absence of the normal ALL-1 transcript in the gastric carcinoma cell line. To determine whether the altered RNA was derived from a partially duplicated ALL-1 gene, RT-PCR was performed on Mgc8O-3 total RNA using oligonucleotide primers from exon 5 in forward orientation (primer 5-1) and from exon 3 in reverse orientation (primer 3.1c) specific for the ALL-1 duplication. An amplified band of the predicted size was detected. Sequence analysis of the nested PCR product showed an in-frame fusion or exon 8 with exon 2. To define the mechanism of the partial duplication of the ALL-1 gene, the two rearranged bands detected by probes B859 and SAS1 were cloned: the 3.8 kb B859 EcoR1 fragment (E3-15) and the 12.5 kb SAS1 BglII fragment (B4M). The two genomic DNA clones were isolated and analyzed by restriction enzyme analysis and DNA sequencing. The sequence of the whole E3-15 clone showed that the breakpoint was in intron 8, 876 bps downstream from exon 8. The last 727 bps of the 3' end of the E3-15 Clone did not show any homology with known genes. The sequence of the subcloned Xbal fragment of the B4M clone showed at the 3' of this clone the SAS1 sequence followed by exon 2-intron 2 and part of the exon 3 of the normal ALL1 gene. Nevertheless, the BamH1 restriction site normally located 5.8 kb upstream of the exon 2 was not detected by restriction analysis of the B4M lambda clone. Two oligonucleotide primers (B1-T3F; 0.9K-F1) were designed in an attempt to close the gap between the E3-15 and B4M clones by amplification. The PCR analysis was performed using as templates the Mgc8O-3 genomic DNA, the DNA of the hybrid 7300 containing a chromosome 11, the DNA of the cos 20 cosmid containing the entire intron 1 of the ALL-1 gene and normal human DNA as a control (Gu, Y., et. al. (1992) *Cell* 71, 701–708, which is incorporated herein by reference). Surprisingly a strong band of the estimated size of 2 kb (MCH1) was detected in only the Mgc8O-3 DNA and in the normal human DNA. To identify the chromosomal location of the MCH1 fragment a further PCR analysis was performed with the same set of primers (B1-T3F; 0.9K-F1) on a panel of somatic hybrids covering all human chromosomes. The result revealed that the fragment interposed between intron 8 and intron 1 of the ALL-1 gene derived from chromosome 1p31.2-32.3. The MCH1 fragment was cloned and sequenced. A Fasta database search against GenBank did not reveal any homology with known DNA sequences.

This study represents the first demonstration of ALL-1 gene alteration and self-fusion in malignant cells derived from a solid tumor. In this gastric adenocarcinoma derived cell line, the ALL-1 gene underwent a partial duplication of the region involving exon 2 through exon, 8 with the interposition of a piece of chromosome 1p31.3-32.1 (MCH1) between intron 8 and the duplicated exon 2. The sequence of the cloned cDNA showed a fusion of exon 8 to exon 2. indicating that the interposed MCH1 fragment of chromosome 1 was spliced out.

I claim:

1. A method of determining whether a solid tumor has an ALL-1 gene rearrangement comprising the steps of:

obtaining a sample of a solid tumor;

contacting a probe or primer which comprises from at least 20 nucleotides to the full length of ALL-1 cDNA or genomic sequence with nucleic acid from a cell in said sample: and detecting the presence of an ALL-1 gene rearrangement in a cell in said sample.

2. A method of determining whether a solid tumor has an ALL-1 gene rearrangement by Southern blot analysis, in situ hybridization analysis, or Northern blot analysis, comprising the steps of:

obtaining a sample of a solid tumor;

hybridizing a probe comprising from at least 20 nucleotides to the full length of ALL-1 cDNA or genomic sequence to nucleic acid from a cell in said sample; and detecting the presence of said probe hybridized to nucleic acid molecules of said sample.

3. The method of claim 2 wherein the presence of an ALL-1 gene rearrangement is detected by Southern blot analysis.

4. The method of claim 3 wherein the presence of an ALL-1 gene rearrangement is detected by Southern blot analysis comprising the steps of:

a) extracting genomic DNA from cells of said sample;

b) digesting said genomic DNA with at least one restriction endonuclease;

c) separating fragments generated by digestion of said genomic DNA in an electrophoresis matrix;

d) fixing said separated DNA to a solid phase;

e) contacting the probe with said DNA fixed to said solid phase; wherein said probe is labelled and is a fragment of cDNA consisting of 100–10,000 nucleotides from the ALL-1 gene or a fragment of genomic DNA consisting of 100–8000 nucleotides from the ALL-1 gene; and, f) comparing the location and/or pattern of hybridization of said probe to fixed digested DNA to the location and/or pattern of hybridization of said probe to fixed digested cellular DNA that does not contain an ALL-1 gene rearrangement.

5. The method of claim 4 wherein said restriction enzyme is BamHI and said probe is B859.

6. The method of claim 2 wherein said probe is a fragment of cDNA consisting of 100–1000 nucleotides from the ALL-1 gene.

7. The method of claim 2 wherein said probe is a fragment of genomic DNA consisting of 100–1000 nucleotides from the ALL-1 gene.

8. The method of claim 2 wherein the presence of an ALL-1 gene rearrangement is detected by Northern blot analysis.

9. The method of claim 8 wherein the presence of an ALL-1 gene rearrangement is detected by Northern blot analysis comprising the steps of:

a) extracting RNA from cells of said sample:

b) separating said RNA in an electrophoresis matrix;

c) fixing said separated RNA to a solid phase;

d) contacting the probe and said RNA fixed to said solid phase; wherein said probe is labelled and is a fragment of cDNA consisting of 100–1000 nucleotides from the ALL-1 gene; and, e) comparing the location and/or pattern of hybridization of said probe to fixed RNA with the location and/or pattern of hybridization of said probe to fixed RNA transcribed from DNA that does not contain a rearrangement of the ALL-1 gene.

10. The method of claim 9 wherein said probe is B859.

11. The method of claim 2 wherein the presence of an ALL-1 gene rearrangement is detected by in situ hybridization.

12. A method of determining whether a solid tumor has an ALL-1 gene rearrangement by in situ hybridization analysis, comprising the steps of:

a) isolating nuclei or chromosomes from cells in said sample;

b) contacting said nuclei or chromosomes with a set of fluorescent marker-labelled oligonucleotide probes, each comprising from at least 20 nucleotides to the full length of ALL-1 cDNA or genomic sequence; said set of probes comprising:

i) a first probe comprising a nucleotide sequence complementary to the ALL-1 gene between the translocation breakpoint region and the centromere; and ii) a second probe comprising a nucleotide sequence complementary to the ALL-1 gene between the translocation breakpoint region and the telomere;

said first probe comprises a fluorescent marker that is distinguishable from a fluorescent marker label of said second probe; and c) observing said chromosomes or nuclei.

13. A method of determining whether a solid tumor has an ALL-1 gene mutation comprising the steps of:

obtaining a sample of a solid tumor;

contacting a probe or primer which comprises from at least 20 nucleotides to the full length of ALL-1 cDNA or genomic sequence with nucleic acid from a cell in said sample; and detecting the presence of an ALL-1 gene mutation in a cell in said sample by DNA sequence analysis.

14. The method of claim 13 wherein the presence of an ALL-1 gene mutation is detected by DNA sequence analysis comprising the steps of:

a) extracting genomic DNA from cells of said sample:

b) amplifying an ALL-1 nucleotide sequence from an ALL-1 exon or cDNA generated from ALL-1 RNA;

c) determining the nucleotide sequence of the amplified DNA; and d) comparing the nucleotide sequence of the amplified DNA to the nucleotide sequence of a normal ALL-1 gene nucleotide sequence.

15. The method of claim 14 wherein the amplified DNA is amplified from an ALL-1 exon.

16. The method of claim 14 wherein the amplified DNA is amplified from cDNA generated from ALL-1 RNA.

17. A method of determining whether a solid tumor has an ALL-1 gene rearrangement by Southern blot analysis, in situ hybridization analysis, or Northern blot analysis, comprising the steps of:

obtaining a sample of a solid tumor;

hybridizing a probe consisting from at least 20 nucleotides to the full length of ALL-1 cDNA or genomic sequence to nucleic acid from a cell in said sample; and detecting the presence of said probe hybridized to nucleic acid molecules of said sample.

18. The method of claim 17 wherein the presence of an ALL-1 gene rearrangement is detected by Southern blot analysis.

19. The method of claim 17 wherein said probe is a fragment of cDNA consisting of 100–1000 nucleotides from the ALL-1 gene.

20. The method of claim 17 wherein said probe is a fragment of genomic DNA consisting of 100–1000 nucleotides from the ALL-1 gene.

21. The method of claim 17 wherein the presence of an ALL-1 gene rearrangement is detected by Northern blot analysis.

22. The method of claim 17 wherein the presence of an ALL-1 gene rearrangement is detected by in situ hybridization.

23. A method of determining whether a solid tumor has an ALL-1 gene rearrangement by in situ hybridization analysis, comprising the steps of:

a) isolating nuclei or chromosomes from cells in said sample;

b) contacting said nuclei or chromosomes with a set of fluorescent marker-labelled oligonucleotide probes, each comprising from at least 20 nucleotides to the full length of ALL-1 cDNA or genomic sequence; said set of probes comprising:

i) a first probe consisting of a nucleotide sequence complementary to the ALL-1 gene between the translocation breakpoint region and the centromere; and ii) a second probe consisting of a nucleotide sequence complementary to the ALL-1 gene between the translocation breakpoint region and the telomere;

said first probe comprises a fluorescent marker that is distinguishable from a fluorescent marker label of said second probe; and c) observing said chromosomes or nuclei.

* * * * *